United States Patent [19]

Wachter

[11] 4,066,681

[45] Jan. 3, 1978

[54] THIOL- AND THIONCARBAMATES AND PROCESS FOR PREPARING SAME

[75] Inventor: Michael P. Wachter, Bloomsbury, N.J.

[73] Assignee: Ortho Pharmaceutical Corporation, Raritan, N.J.

[21] Appl. No.: 645,496

[22] Filed: Dec. 31, 1975

[51] Int. Cl.$^2$ .................. C07C 155/09; C07C 155/08
[52] U.S. Cl. ............................ 260/455 A; 260/304 R; 260/347.2; 424/270; 424/285; 424/300
[58] Field of Search .................................. 260/455 A

[56] References Cited

U.S. PATENT DOCUMENTS

| | | | |
|---|---|---|---|
| 2,723,989 | 11/1955 | Harman | 260/455 A |
| 3,330,643 | 7/1967 | Harman et al. | 260/455 A |
| 3,687,653 | 8/1972 | Bollinger et al. | 260/455 A |
| 3,719,702 | 3/1973 | Traber et al. | 260/455 A |
| 3,742,007 | 6/1973 | Osieka et al. | 260/455 A |
| 3,953,427 | 4/1976 | Matolcsy et al. | 260/455 A |

FOREIGN PATENT DOCUMENTS

| | | | |
|---|---|---|---|
| 1,310,953 | 10/1962 | France | 260/455 A |
| 4,315,965 | 4/1965 | Japan | 260/455 A |
| 4,314,452 | 4/1965 | Japan | 260/455 A |

OTHER PUBLICATIONS

J. Amer. Chem. Soc., vol. 31, (1966), pp. 3980-3984.
Chem. Abst., vol. 76, (1972), p. 55125u.
Chem. Abst., vol. 49, (1955), p. 2329.
J. Amer. Chem. Soc., vol. 78, (1955), pp. 844-847.
J. Amer. Chem. Soc., vol. 81, (1958), pp. 714-727.

*Primary Examiner*—Delbert R. Phillips
*Attorney, Agent, or Firm*—Benjamin F. Lambert

[57] ABSTRACT

Thiol- and thioncarbamates are described. The thiol- and thioncarbamates are useful as antifertility agents.

1 Claim, No Drawings

THIOL- AND THIONCARBAMATES AND PROCESS FOR PREPARING SAME

This invention relates to certain thiol- and thioncarbamates which are active antifertility agents. The compounds exhibit both post-implantive and pre-implantive activity and are useful in the suppression of reproduction in female animals.

Certain thiol- and thioncarbamates are known in the art, but prior to the present invention, no pharmaceutical activity for these compounds has been described. The present invention describes certain thiol- and thioncarbamates which have been found to have useful acitivity as antifertility agents. In addition to the known compounds, certain novel thiol- and thioncarbamates are disclosed which are active antifertility agents.

The compounds which are the subject of this invention are represented by the following formulae:

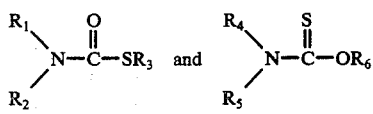

wherein
R$_1$ is lower alyl having 1–10 carbon atoms such as, for example, methyl, butyl, pentyl, heptyl, nonyl and the like, lowr alkenyl having 2–10 carbon atoms such as, for example, ethenyl, propenyl, butenyl, hexenyl, octenyl and the like, phenyl, substituted phenyl such as nitrophenyl, halophenyl, lower alkoxy phenyl wherein the alkoxy group has 1–5 carbons, benzyl, lower alkoxy benzyl wherein the alkoxy group has 1–5 carbons, lower alkoxyalkyl having 2–8 carbon atoms, dicyclopentadienyl, adamantyl and cycloalkyl having 3–6 carbon atoms such as cyclopropyl, cyclobutyl, cyclopentyl and the like;

R$_2$ is hydrogen or lower alkyl having 1–10 carbon atoms;

R$_1$ and R$_2$ together are an amino radical having 4–12 carbon atoms such as, for example, 2-oxo-dihydrobenzothiazo-3-yl, morpholino, pyrrolidino, piperidino, indolinyl, or diphenylamino.

R$_3$ is alkyl having 1–16 carbon atoms, lower alkenyl having 2–10 carbon atoms, furfuryl, phenyl, phenylalkyl wherein the alkyl group has 1–3 carbon atoms, triphenylmethyl and cycloalkyl wherein the alkyl group has 3–6 carbon atoms;

R$_4$ is lower alkyl having 1–10 carbon atoms, phenyl, substituted phenyl such as halophenyl, nitrophenyl, trifluoromethyl phenyl, lower alkoxy phenyl wherein the alkoxy group has 1–5 carbon atoms and the like;

R$_5$ is hydrogen or lower alkyl having 1–10 carbon atoms; and

R$_6$ is lower alkyl having 1–10 carbon atoms.

Although all of the compounds of the present invention are useful in the suppression of reproduction, those compounds of the present invention which are novel compounds are represented by the formulae:

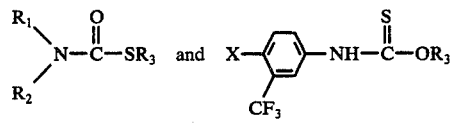

wherein
R$_1$ is lower alkyl having 1–10 carbon atoms, isobutenyl, halophenyl, dicyclopentadienyl, adamantyl and cycloalkyl having 3–6 carbon atoms;

R$_2$ is hydrogen;

R$_3$ is alkyl having 1–16 carbon atoms, lower alkenyl having 2–10 carbon atoms, furfuryl, phenyl, triphenylmethyl, cycloalkyl wherein the alkyl group has 3–6 carbon atoms, R$_1$ and R$_2$ together are 2-oxo-dihydrobenzothiazo-3-yl and X is halogen provided that where R$_1$ is lower alkyl, R$_3$ is other than lower alkyl.

Of the novel compounds of this invention, the preferred compounds are those wherein R$_1$ is lower alkyl having 1–5 carbon atoms, isobutenyl, m-chlorophenyl, dicyclopentadienyl, adamantyl and cyclopropyl; R$_2$ is hydrogen; R$_3$ is alkyl having 1–16 carbon atoms, lower alkenyl having 2–5 carbon atoms, furfuryl, phenyl, triphenylmethyl and cyclopropyl; R$_1$ and R$_2$ together are 2-oxo-dihydrobenzothiazo-3-yl and X is chloro.

The thiol- and thioncarbamates can be prepared by treating an alkyl or aryl isothiocyanate with the appropriate alkali metal alkoxide, such as sodium ethoxide, for example, in a suitable solvent. The reaction may be carried out at room temperature, but it is preferred to carry out the reaction at the reflux temperature of the solvent employed. Suitable solvents include lower alkanols such as ethanol, propanol, butanol and the like. The alkali metal intermediate compound is then treated with acid to obtain the corresponding thioncarbamate. Mineral acids such as hydrochloric acid, hydrobromic acid, sulfuric acid and nitric acid may be employed. The thiolcarbamate is prepared by treating the thioncarbamate with an excess of the corresponding alkyl iodide. Examples of suitable alkyl iodides include ethyl iodide, methyl iodide and the like. The reaction is preferably carried out at elevated temperatures. The preferred temperature range is 50°–150° depending upon the solvent employed. The thion- and thiolcarbamates are isolated by techniques known to those skilled in the art.

Alternatively the thiolcarbamates can be prepared by treating an alkyl halothiolformate, such as ethyl chlorothiolformate, with an appropriate amine in a suitable solvent. The reaction can be carried out at a temperature between 0°–10° C; however, it is preferred to carry out the reaction at about 0° C. Suitable solvents include lower alkyl ethers such as diethyl ether, tetrahydrofuran, dioxane, diethylene glycol diethyl ether and the like. After the initial reaction is complete, the mixture is generally stirred at room temperature to ensure the maximum yield of the desired compound. The thiolcarbamate is collected by methods known to those skilled in the art.

A third method of preparing the thiolcarbamates comprises treating an alkyl or aryl isocyanate with the appropriate mercaptan. The reaction is generally carried out at room temperature in the presence of a base such as pyridine, triethylamine or 1,4-diazabicyclo[2,2,2] octane for example. In those cases where one of the reactants is a solid, a suitable solvent such as dimethylformamide or dimethylsulfoxide may be employed.

The thioncarbamates can also be prepared by treating an appropriately substituted aryl amine with thiophosgene. The aryl isothiocyanate intermediate is then treated with an alkali metal alkoxide such as sodium ethoxide, for example, in a suitable solvent such as a lower alkanol to afford the desired aryl thioncarbamate.

The thiol- and thioncarbamates of the present invention possess valuable pharmacological activity as anti-littering agents. They are useful, therefore, as agents for the suppression of reproduction. The compounds can be administered orally to female animals and have post-implantive and pre-implantive activity. Treatment on the first 12 days of gestation generally resulted in complete inhibition of fertility; in such cases no implantation sites were observable. In most cases when treatment was initiated after implantation, resorptions occurred. The compounds are active at dose levels ranging from about 10 mg./kg. to about 300 mg./kg. The preferred dosage range is from about 20 to about 150 mg./kg.

The antifertility activity of the compounds is determined as follows:

Adult female Wistar rats are smeared daily and cohabited continuously with males of proven fertility. Each morning the females are examined for the presence of sperm in vaginal washings. The day on which sperm are found constitutes day 1 of pregnancy. Pregnant rats receive the test compound dissolved in sesame oil by gavage on day 1 through day 6 of pregnancy for studies of anti-implantive activity or on days 7 through 12 for studies of post-implantive effects. They are sacrificed on day 20 for examination of uterine contents. The number of implantations and their appearance are recorded. Controls receive only the vehicle.

EXAMPLE 1

Isopropyl N-methylthiolcarbamate

Methylisothiocyanate (10.95 g., 0.15 m.) is added to a refluxing solution of sodium isopropoxide (0.15 m.) in 125 ml. of isopropanol. The reaction mixture is refluxed for 3 hrs. after which the isopropanol is evaporated in vacuo. Ether (400 ml.) is added to the residue; the resulting solid is filtered, treated with dilute hydrochloric acid and extracted with ether. Upon removal of the ether, S-isopropyl-N-methylthioncarbamate is obtained, yield 17.3 g. (86%). A solution of the thioncarbamate (10 g.) and isopropyl iodide (22 g.) are heated at 95° C for 4 hrs. The excess isopropyl iodide is evaporated in vacuo. Distillation of the residue gave isopropyl-N-methylthiolcarbamate, yield 4.0 g. (40%); b.p. 98°–99°/12 mm.

Those compounds wherein R₂ is other than hydrogen are prepared by first reacting thiocarbamoyl chloride with the corresponding amine. The reaction product is then treated with a metal alkoxide to form a thioncarbamate and then with an alkyl iodide to form the corresponding thiolcarbamate as described above.

The following examples were prepared by the method of Example 1 substituting for methylisothiocyanate and sodium isopropoxide equivalent amounts of the appropriate alkyl or aryl isothiocyanate and metal alkoxide:

| Example | R₁ | R₂ | R₃ | M.P./B.P. |
|---|---|---|---|---|
| 2 | CH₃— | CH₃ | C₂H₅— | 76–77°/15 mm. |
| 3 | CH₃— | H | C₂H₅— | 100–101°/15 mm. |

-continued

| Example | R₁ | R₂ | R₃ | M.P./B.P. |
|---|---|---|---|---|
| 4 | 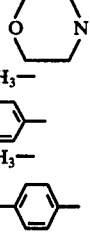 | | C₂H₅— | 137°/15 mm. |
| 5 | CH₃— | H | n-C₄H₉— | 40–41° C |
| 6 | C₆H₅— | H | C₂H₅— | 64° C |
| 7 | CH₃— | H | (CH₃)₂CH— | 98–99°/12 mm. |
| 8 | F-C₆H₄— | H | C₂H₅— | 70° C |

EXAMPLE 9

Ethyl-exo-5-N-(5,6-dihydro-endo-dicyclopentadienyl)-thiolcarbamate

A solution of ethyl chlorothiolformate (4.05 g., 32.5 mM.) in 10 ml. of ether is added dropwise to a solution of exo-5-amino-5,6-dihydro-endo-dicyclopentadiene (9.7 g., 65 mM.) in 100 ml. of ether while maintaining the temperature at 0°–5° C. The resulting suspension is warmed to room temperature and stirred for 1 hr. The amine salt which forms is filtered and washed with ether, and the filtrates are evaporated to afford 7.1 g. of a brown crystalline solid. Recrystallization from toluene:petroleum ether gives ethyl-N-β-dicyclopentadienylthiolcarbamate as a light brown powder, yield 3.2 g. (42%).

The following compounds are prepared by the method of Example 9 substituting for ethyl chlorothiolformate and exo-5-amino-5,6-dihydroendo-dicyclopentadiene equivalent amounts of the appropriate alkyl halothiolformate and amine:

| Example | R₁ | R₂ | R₃ | M.P./B.P. |
|---|---|---|---|---|
| 10 | CH₃OCH₂CH₂— | H | C₂H₅— | 80–85/1 mm. |
| 11 | CH₂=CH—CH₂— | H | C₂H₅— | 135–37°/29 mm. |
| 12 | CH₂=CH—CH(CH₃)— | H | C₂H₅— | 62°/1 mm. |
| 13 | dicyclopentadienyl | H | C₂H₅— | 109° C |
| 14 | 1-adamantyl | H | C₂H₅— | 120° C |
| 15 | CH₃O—C₆H₄—CH | | H | C₂H₅ | 77–78° C |
| 16 | CH₃— | H | n-C₃H₇— | 71°/12.5 mm. |
| 17 | CH₃— | H | C₆H₅— | 101° C |
| 18 | (CH₃)₂CHCH(CH₃)— | H | C₂H₅— | 82°/1.25 mm. |
| 19 |  | | H | C₃H₇— | 143–44°/12 mm. |
| 20 |  | | H | CH₃— | 56° C |
| 21 |  | | H | C₂H₅— | 46° C |
| 22 |  | | H | C₆H₅— | 80° C |
| 23 | H | | H | C₂H₅— | 105° C |

EXAMPLE 24

Ethyl N-m-chlorophenylthiolcarbamate

A solution of m-chlorophenylisocyanate (7.68 g., 50 mM.), ethanethiol (3.1 g., 50 mM.) and anhydrous pyridine (0.25 ml.) is allowed to stir at room temperature. After 2 hrs. the solution begins to solidify and stirring is continued for 16 hrs. The solid is filtered off and recrystallized from toluene:petroleum ether to afford ethyl-N-m-chlorophenylthiolcarbamate, yield 10.1 g. (92%), m.p. 68°-70°.

The following compounds are prepared by the method of Example 24 substituting for m-chlorophenylisocyanate and ethanethiol equivalent amounts of the appropriate alkyl or aryl isocyanate and mercaptan:

| Example | $R_1$ | $R_2$ | $R_3$ | M.P./B.P. |
|---|---|---|---|---|
| 25 | $CH_3$— | H | —$CH_2$— | 46–47° C |
| 26 | Cl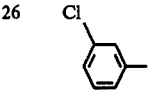— | H | —$C_2H_5$ | 68–70° C |
| 27 | $CH_3$— | H | —$CH_2$— | 55–57° C |
| 28 | $CH_3$— | H |  | 86–87° C |
| 29 | $CH_3$— | H | —$CH_2(CH_2)_{14}CH_3$ | 67–68° C |
| 30 | $CH_3$— | H | —$CH(CH_3)$— | 6.25° C |
| 31 | $CH_3$— | H | —$CH_2$—$CH=CH_2$ | 82–84°/1 mm. |
| 32 | $CH_3$— | H | —C—$_3$ | 149° C |

EXAMPLE 33

Ethyl N-3,4-dichlorophenylthioncarbamate 3,4-Dichloroaniline (19.44 g., 120 mM.) is added with vigorous stirring to a solution of thiophosgene in $H_2O$ (100 ml.) while maintaining the temperature at 15° C during the addition. The reaction is allowed to warm slowly to room temperature and is stirred for 1 hr. The aqueous layer is separated and extracted with 3 × 50 ml. $CHCl_3$; the combined organic layers are dried over $CaCl_2$ and filtered. The filtrate is evaporated in vacuo to give 3,4-dichlorophenylisothiocyanate (20.5 g.) which is used without purification in the next step.

3,4-Dichlorophenylisothiocyanate (20.5 g., 100 mM.) is added to a solution of NaOEt (110 mM.) in EtOH [generated in situ from Na (2.55 g., 110 mM.) and 200 ml. of EtOH] at room temperature. The reaction is allowed to stir at room temperature for 1.5 hrs. and is then warmed to 45° C for 0.5 hr. The EtOH is evaporated in vacuo, 250 ml. of anhydrous ether is added followed by 150 ml. of cold 10% HCl. The layers are separated; the aqueous layer is re-extracted with 3 × 100 ml. ether and the combined ethereal extracts are treated with charcoal, filtered and evaporated in vacuo to give a yellow solid. Recrystallization from benzene-hexane gives ethyl N-3,4-dichlorophenylthioncarbamate, yield = 13.1 g. (44%); m.p. = 125°.

The following examples are prepared by the method of Example 33 substituting for 3,4-dichloroaniline an equivalent amount of the appropriately substituted aryl amine:

| Example | $R_4$ | $R_5$ | $R_6$ | M.P./B.P. |
|---|---|---|---|---|
| 34 | Cl—— | H | $C_2H_5$— | 106° C |
| 35 | $CH_3O$—— | H | $C_2H_5$— | 79° C |
| 36 | Cl—($CF_3$)— | H | $C_2H_5$— | 129° C |

The following compounds are prepared by reacting an isothiocyanate with the appropriate alkali metal alkoxide followed by acid treatment following the procedure of Example 1 up to but not including the reaction with the alkyl iodide.

| Example | $R_4$ | $R_5$ | $R_6$ | M.P./B.P. |
|---|---|---|---|---|
| 37 | $CH_3$— | $CH_3$— | $C_2H_5$— | 83°/16 mm. |
| 38 | $CH_3$— | H | $C_2H_5$— | 96°/15 mm. |
| 39 | — | H | $C_2H_5$— | 63° C |
| 40 | $O_2N$—— | H | $C_2H_5$— | 179° C |
| 41 | F—— | H | $C_2H_5$— | 85–87° C |

EXAMPLE 42

3-(Ethyl thiolformyl)-benzothiazolin-2-one

Benzothiazolidinone (4.53 g., 30 mM.) is dissolved in benzene (125 ml.); small pieces of sodium are added (0.70 g., 30.5 mM.) with vigorous stirring and the resulting suspension is refluxed for 1 hr. Glycol monomethyl ether (1.5 ml.) is added and the suspension is stirred an additional 30 mins. Ethyl chlorothiolformate (3.8 g., 30.5 mM.) in 25 ml. of benzene is added over 10 minutes and the suspension is stirred rapidly at reflux for 1.5 hrs., cooled and filtered. The filter cake is washed with benzene and the filtrate is washed with 3 × 50 ml. $H_2O$, dried over $MgSO_4$ and evaporated in vacuo to give a semi-solid which upon recrystallization from benzene-petroleum ether gives 1.1 g. of unreacted benzothiazolidinone. The filtrate is evaporated in vacuo to give a yellow oil. The oil is distilled under reduced pressure and the material distilling at 85°/0.5 mm. is removed. The residue is crystallized from petroleum ether to give 1.45 g. of 3-(ethyl thiolformyl)-benzothiazolin-2-one), 27% yield based on recovered starting material, m.p. 55°-56°.

What is claimed is:
1. Ethyl-exo-5-N-(5,6-dihydro-endo-dicyclopentadienyl)-thiolcarbamate.

* * * * *

UNITED STATES PATENT AND TRADEMARK OFFICE
CERTIFICATE OF CORRECTION

PATENT NO. : 4,066,681

DATED : January 3, 1978

INVENTOR(S) : Michael P. Wachter

It is certified that error appears in the above-identified patent and that said Letters Patent are hereby corrected as shown below:

Column 1, Line 30, "lower alyl" should be -- lower alkyl --.
    Column 1, Line 32, "lowr alkenyl" should be -- lower alkenyl --.
    Column 2, Line 23, "m-chlorophenyl" should be -- m-chlorophenyl --.
    Column 3, Line 20, "about 20 to" should be -- about 20 mg./kg. to --.
    Column 3, Lines 42-43, "in vacuo" should be underscored.
    Column 3, Lines 49-50, "in vacuo" should be underscored.
    Column 4, Line 49, Example 15,

 should be

--  --.

Column 5, Line 3, Example 24, "m" should be underscored.
    Column 5, Line 4, Example 24, "m" should be underscored.
    Column 5, Lines 10 and 14, "m" should be underscored.
    Column 5, Line 31, Example 30, "6.25°C." should be -- 62.5°C. --.
    Column 5, Line 49, "in vacuo" should be underscored.
    Column 5, Line 54, "in situ" should be underscored.

UNITED STATES PATENT AND TRADEMARK OFFICE
CERTIFICATE OF CORRECTION

PATENT NO. : 4,066,681
DATED : January 3, 1978
INVENTOR(S) : Michael P. Wachter

It is certified that error appears in the above-identified patent and that said Letters Patent are hereby corrected as shown below:

Column 5, Lines 59 and 64, "in vacuo" should be underscored.
Column 6, Lines 51 and 54, "in vacuo" should be underscored.

Signed and Sealed this

Seventh Day of November 1978

[SEAL]

Attest:

RUTH C. MASON
Attesting Officer

DONALD W. BANNER
Commissioner of Patents and Trademarks